US00PP15968P2

(12) United States Plant Patent
Mallet

(10) Patent No.: US PP15,968 P2
(45) Date of Patent: Sep. 20, 2005

(54) ***HYDRANGEA* PLANT NAMED 'CLAUDIE'**

(50) Latin Name: *Hydrangea macrophylla*
Varietal Denomination: Claudie

(75) Inventor: Corrine Mallet, Varengeville S'Mer (FR)

(73) Assignee: Spring Meadow Nursery, Inc., Grand Haven, MI (US)

( * ) Notice: Subject to any disclaimer, the term of this patent is extended or adjusted under 35 U.S.C. 154(b) by 68 days.

(21) Appl. No.: 10/882,873

(22) Filed: Jul. 1, 2004

(51) Int. Cl.[7] ..... A01H 5/00
(52) U.S. Cl. ..... Plt./250
(58) Field of Search ..... Plt./250

*Primary Examiner*—Anne Marie Grunberg
(74) *Attorney, Agent, or Firm*—C. A. Whealy

(57) ABSTRACT

A distinct cultivar of *Hydrangea* plant named 'Claudie', characterized by its upright and outwardly spreading plant habit; glossy foliage; inflorescences held upright and outward on strong stems; lacecap-type inflorescences; and numerous fertile flowers per inflorescence and large showy sepals on the sterile flowers.

2 Drawing Sheets

Botanical classification/cultivar designation: *Hydrangea macrophylla* cultivar Claudie.

BACKGROUND OF THE INVENTION

The present Invention relates to a new and distinct cultivar of *Hydrangea* plant, botanically known as *Hydrangea macrophylla*, and hereinafter referred to by the cultivar name Claudie.

The new *Hydrangea* originated from a cross-pollination during the spring of 1997 of a unnamed selection of *Hydrangea macrophylla*, not patented, as the female, or seed, parent with an unknown selection of *Hydrangea macrophylla*, not patented, as the male, or pollen, parent. The cultivar Claudie was discovered and selected by the Inventor as a single plant within the progeny of the stated cross-pollination in a controlled environment in Varengeville S'mer, France.

Asexual reproduction of the new cultivar by softwood cuttings in Varengeville S'mer, France since the summer of 1999, has shown that the unique features of this new *Hydrangea* are stable and reproduced true to type in successive generations.

SUMMARY OF THE INVENTION

Plants of the cultivar Claudie have not been observed under all possible environmental conditions. The phenotype may vary somewhat with variations in environment such as temperature and light intensity without, however, any variance in genotype.

The following traits have been repeatedly observed and are determined to be the unique characteristics of 'Claudie'. These characteristics in combination distinguish 'Claudie' as a new and distinct cultivar:

1. Upright and outwardly spreading plant habit.
2. Glossy foliage.
3. Inflorescences held upright and outward on strong stems.
4. Lacecap-type inflorescences.
5. Numerous fertile flowers per inflorescence and large showy sepals on the sterile flowers.

Plants of the new *Hydrangea* differ from plants of female parent selection in the following characteristics:

1. Flower sepals of plants of the new *Hydrangea* are narrower than flower sepals of plants of the female parent selection.
2. Flower sepals of plants of the new *Hydrangea* are widely-spaced and do not overlap whereas flower sepals of plants of the female parent selection are overlapping.

Plants of the new *Hydrangea* can be compared to plants of the *Hydrangea macrophylla* cultivar Mousmee, not patented. In side-by-side comparisons conducted in Grand Haven, Mich., plants of the new *Hydrangea* differed from plants of the cultivar Mousmee in the following characteristics:

1. Plants of the new *Hydrangea* are shorter than plants of the cultivar Mousmee.
2. Plants of the new *Hydrangea* have shorter internodes than plants of the cultivar Mousmee.
3. Plants of the new *Hydrangea* are not as freely flowering as plants of the cultivar Mousmee.
4. Flower sepals of plants of the new *Hydrangea* are narrower than flower sepals of plants of the cultivar Mousmee.
5. Flower sepals of plants of the new *Hydrangea* are widely-spaced and do not overlap whereas flower sepals of plants of the cultivar Mousmee are overlapping.
6. Plants of the new *Hydrangea* have lighter colored flower sepals than plants of the cultivar Mousmee.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea*.

The photograph on the first sheet is a side perspective view of a typical plant of 'Claudie'.

The photograph on the second sheet comprises a close-up view of a typical inflorescence of 'Claudie'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. Plants were about four years old when the photographs and description were taken and the pH level of the soil was about 6.5. Photographs and description were taken during the summer and fall when the plants were in full flower.

Botanical classification: *Hydrangea macrophylla* cultivar Claudie.

Parentage:

*Male, or pollen, parent.*—Unnamed selection of *Hydrangea macrophylla*, not patented.

*Female, or seed, parent.*—Unknown *Hydrangea macrophylla* selection, not patented.

Propagation:

*Type cutting.*—By softwood cuttings.

*Time to initiate roots.*—About ten days at 23° C.

*Time to produce a rooted cutting or liner.*—About two months at 23° C.

*Root description.*—Fine, fibrous; creamy white in color.

*Rooting habit.*—Freely branching.

Plant description:

*Form/growth habit.*—Upright and outwardly spreading plant habit; round in overall shape; dense and bushy perennial shrub. Vigorous growth habit.

*Plant height, soil level to top of plant plane.*—About 80 cm.

*Plant diameter or area of spread.*—About 84 cm.

*Branching habit.*—Freely branching, about 18 lateral branches per plant. Pruning will enhance branching potential.

*Lateral branches.*—Length: About 27 cm. Diameter: About 6 mm. Internode length: About 4.5 cm. Texture: Smooth, glabrous. Color: 143C.

*Foliage description.*—Arrangement: Opposite, simple. Length: About 17 cm. Width: About 10 cm. Shape: Ovate. Apex: Acute. Base: Obtuse to cuneate. Margin: Serrate. Texture, upper and lower surfaces: Thick, leathery; glabrous; rugose. Venation pattern: Pinnate. Color: Developing and fully expanded foliage, upper surface: 146A; glossy. Developing and fully expanded foliage, lower surface: 146B. Venation, upper surface: 145B. Venation, lower surface: 145C. Petiole: Length: About 2.2 cm. Diameter: About 4 mm. Texture, upper and lower surfaces: Smooth, glabrous. Color, upper and lower surfaces: 145C.

Flower description:

*Flower type and habit.*—Single fertile and sterile flowers arranged on terminal panicles in a lacecap formation. Sterile flowers with large showy sepals and without petals and reproductive organs. Fertile flowers small with petals, sepals and reproductive organs. Flowers persistent. Flowers not fragrant.

*Natural flowering season.*—Continuously flowering from June until frost in Grand Haven, Mich.

*Flower longevity.*—Sterile flowers last about three months on the plant; fertile flowers last about 26 days on the plant.

*Quantity of flowers.*—Freely flowering; about nine sterile flowers and about 625 fertile flowers per panicle.

*Inflorescence diameter.*—About 21 cm.

*Inflorescence height.*—About 7 cm.

*Flower diameter.*—Fertile flowers: About 6 mm. Sterile flowers: About 6 cm.

*Flower depth (height).*—Fertile flowers: About 4 mm. Sterile flowers: About 3 mm.

*Flower buds (fertile and sterile flowers).*—Length: About 2 mm. Diameter: About 4 mm. Shape: Globose. Color: 144B.

*Petals (petals present only on fertile flowers; sterile flowers do not have petals).*—Quantity per flower: About four. Length: About 3 mm. Width: About 3 mm. Shape: Subulate. Apex: Acute. Base: Truncate. Margin: Entire. Texture, upper and lower surfaces: Smooth, glabrous. Color: When opening and fully opened, upper surface: 72A; color becoming closer to 72C with development. When opening and fully opened, lower surface: 72C.

*Sepals.*—Quantity per flower, fertile and sterile flowers: Fertile flowers: About five, fused into a calyx. Sterile flowers: About four, not fused. Length: Fertile flowers: About 0.5 mm. Sterile flowers: About 3 cm. Width: Fertile flowers: About 0.5 mm. Sterile flowers: About 2.2 mm. Shape: Fertile flowers: Acute with lobation. Sterile flowers: Obovate. Apex: Fertile flowers: Acute. Sterile flowers: Acute to somewhat obtuse. Base: Fertile flowers: Fused. Sterile flowers: Cuneate to attenuate. Margin, fertile and sterile flowers: Entire. Texture, fertile and sterile flowers, upper and lower surfaces: Smooth, glabrous. Color: Fertile flowers: When opening and fully opened, upper surface: 72A. When opening and fully opened, lower surface: 72C. Sterile flowers: When opening, upper surface: 66B. When opening, lower surface: 66C. Fully opened, upper surface: 66C; color becoming closer to 66D with development. Fully opened, lower surface: 66D.

*Peduncles.*—Length: About 6 cm. Diameter: About 4 mm. Angle: About 15° from vertical. Strength: Strong. Texture: Slightly pubescent. Color: 60C.

*Pedicels.*—Length: Fertile flowers: About 5 mm. Sterile flowers: About 4.5 cm. Diameter: Fertile flowers: About 1.5 mm. Sterile flowers: About 1.5 mm. Angle: Fertile flowers: About 15° from vertical. Sterile flowers: About 45° from vertical. Strength: Fertile flowers: Strong. Sterile flowers: Weak to moderately strong. Texture: Fertile flowers: Very slightly pubescent. Sterile flowers: Smooth, glabrous. Color, fertile and sterile flowers: 61B.

*Reproductive organs (reproductive organs present only on fertile flowers; sterile flowers do not have reproductive organs).*—Stamens: Quantity per flower: About eight. Anther shape: Round. Anther length: About 0.75 mm. Anther color: 198D. Pollen amount: Scarce. Pollen color: 198D. Pistils: Pistil quantity per flower: About four. Pistil length: Less than 0.5 mm. Stigma shape: Three-lobed. Stigma color: 61A. Style length: Less than 0.5 mm. Style color: 61A. Ovary color: 186D. Seed: Seed development has not been observed. Fruit: Length: About 7 mm. Diameter: About 4 mm. Texture: Smooth, glabrous. Color: 137C.

Disease/pest resistance: Under commercial production conditions, plants of the new *Hydrangea* have been observed to be resistant to Mildews. Plants of the new *Hydrangea* have not been observed to be resistant to pests or other pathogens common to *Hydrangea*.

Weather tolerance: Plants of the new *Hydrangea* have been shown to be tolerant to temperatures ranging from −25 to 34° C. Flowers of plants have exhibited excellent tolerance to wind and rain.

It is claimed:

1. A new and distinct cultivar of *Hydrangea* plant named 'Claudie', as illustrated and described.

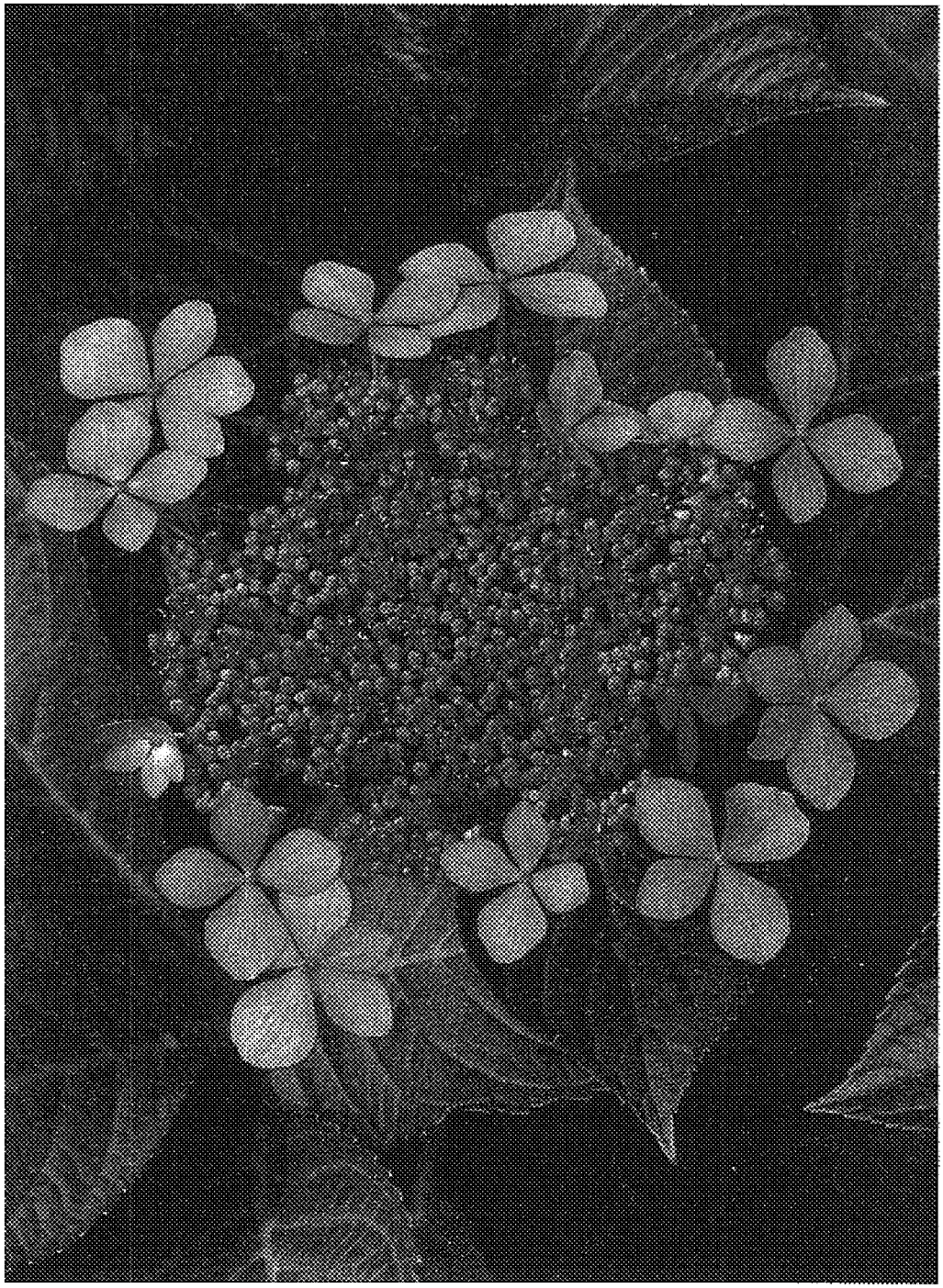

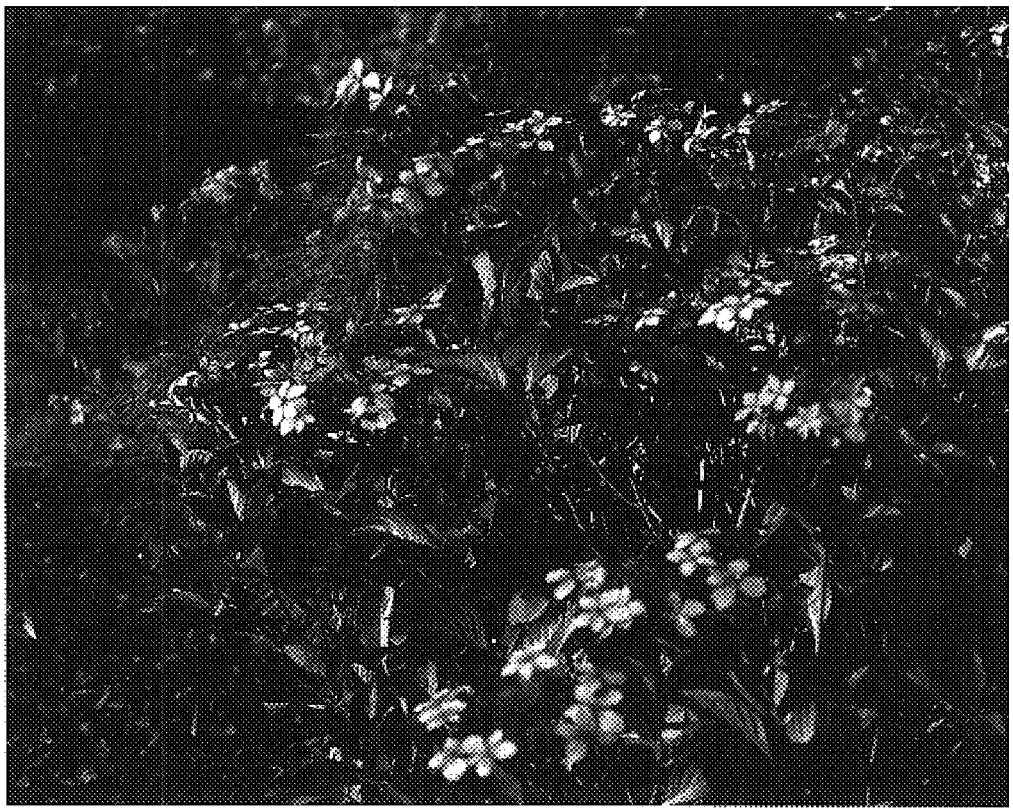

* * * * *